(12) United States Patent
Jenkins et al.

(10) Patent No.: US 7,772,292 B2
(45) Date of Patent: Aug. 10, 2010

(54) SYNTHESIS GAS PRODUCTION AND USE

(75) Inventors: Christopher David William Jenkins, South Caulfield (AU); James R. Lattner, La Porte, TX (US); Michael J. Veraa, Houston, TX (US); Keith H. Kuechler, Friendswood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 746 days.

(21) Appl. No.: 11/786,922

(22) Filed: Apr. 13, 2007

(65) Prior Publication Data
US 2007/0282018 A1    Dec. 6, 2007

Related U.S. Application Data

(60) Provisional application No. 60/810,092, filed on May 31, 2006.

(51) Int. Cl.
C07C 27/00    (2006.01)
C07C 1/00    (2006.01)

(52) U.S. Cl. .................. 518/702; 518/700; 518/703; 518/704

(58) Field of Classification Search .................. 518/700, 518/702, 703, 704; 585/640
See application file for complete search history.

(56) References Cited

U.S. PATENT DOCUMENTS

| 4,782,096 | A | 11/1988 | Banquy |
| 5,252,609 | A | 10/1993 | Pinto |
| 5,310,506 | A | 5/1994 | Supp et al. |
| 5,496,859 | A | 3/1996 | Fong et al. |
| 6,224,789 | B1 | 5/2001 | Dybkjaer |
| 6,402,988 | B1 | 6/2002 | Gottzmann et al. |
| 6,486,219 | B1 | 11/2002 | Janda et al. |
| 2003/0236312 | A1 | 12/2003 | O'Rear |
| 2004/0241086 | A1 | 12/2004 | Van Dongen et al. |

FOREIGN PATENT DOCUMENTS

| EP | 0 522 744 | 1/1993 |
| WO | WO 93/15999 | 8/1993 |
| WO | WO03/029174 | 10/2003 |
| WO | WO2004/092062 | 10/2004 |
| WO | WO2004/092063 | 10/2004 |

OTHER PUBLICATIONS

Aasberg-Petersen et al., "Technologies for large-scale gas conversion," *Applied Catalysis, A: General*, 221 (1-2), pp. 379-387 (2001).

*Primary Examiner*—Jafar Parsa
(74) *Attorney, Agent, or Firm*—Kevin M. Faulkner (57) ABSTRACT

A method of producing synthesis gas for methanol synthesis that comprises the steps of: (a) obtaining a hydrogen stream that has greater than 5 mol % methane from an external process; (b) feeding into a reforming reactor: (i) a feed gas that comprises methane, (ii) water in a specified amount, (iii) oxygen in a specified amount, and (iv) the hydrogen stream in a specified amount; (c) reacting the feed gas, water, oxygen and the hydrogen stream in the reactor; and (d) withdrawing from the reactor the synthesis gas that is at a specific temperature, has less than 3 mol % methane, and has a stoichiometric number of from 1.9 to 2.3.

10 Claims, 4 Drawing Sheets

SYNTHESIS GAS PRODUCTION AND USE

CROSS-REFERENCE TO RELATED APPLICATIONS

This application claims priority to U.S. Provisional Application No. 60/810,092, filed on May 31, 2006.

FIELD OF THE INVENTION

This invention relates to the production and use of synthesis gas (syngas). In particular, this invention relates to the production of syngas using a methane containing hydrogen stream produced from a hydrocarbon conversion process other than the immediate process.

BACKGROUND OF THE INVENTION

Methanol is one of the major chemical raw materials, ranking third in volume behind ammonia and ethylene. Worldwide demand for methanol as a chemical raw material continues to rise especially in view of its increasingly important role (along with dimethyl ether) as a source of olefins such as ethylene and propylene and as an alternative energy source, for example, as a motor fuel additive or in the conversion of methanol to gasoline.

Methanol (as well as dimethyl ether) can be produced via the catalytic conversion of a gaseous feedstock comprising hydrogen, carbon monoxide and carbon dioxide. Such a gaseous mixture is commonly referred to as synthesis gas or "syngas".

Methanol is typically produced from the catalytic reaction of syngas in a methanol synthesis reactor in the presence of a heterogeneous catalyst. For example, in one synthesis process, methanol is produced using a copper/zinc catalyst in a water-cooled tubular methanol reactor. In methanol production, syngas undergoes three reactions, only two of which are independent. These reactions are:

$$2H_2 + CO \leftrightarrow CH_3OH \quad (1)$$

$$3H_2 + CO_2 \leftrightarrow CH_3OH + H_2O \quad (2)$$

$$H_2O + CO \leftrightarrow H_2 + CO_2 \quad (3)$$

As can be seen from Reactions #2 and #3, $CO_2$ can participate in methanol synthesis. Nevertheless, it is desirable to minimize the amount of $CO_2$ in the syngas for several reasons. In the first place, a low $CO_2$ content in the syngas results in a more reactive mixture for methanol synthesis provided the $CO_2$ content is at least about 2%. Furthermore, less $CO_2$ results in lower consumption of hydrogen and lower production of water. Lower water production is useful in applications where some relative small amounts of water can be present in the methanol product such as, for example, in connection with a methanol to olefins (MTO) process. Production of methanol with low water content thus eliminates the need to distill water from the syngas product methanol.

The syngas stoichiometry for methanol synthesis from syngas is generally described by the following relationship known as the "Stoichiometric Number" or $S_N$.

$$S_N = (H_2 - CO_2)/(CO + CO_2) \quad (4)$$

The value of $S_N$ theoretically required for methanol synthesis is 2.0. However, for commercial production of methanol from syngas, it is desirable that the value for $S_N$ range from about 1.95 to 2.15. Dimethyl ether (DME) may also be produced from syngas using chemistry similar to that used for methanol synthesis.

Autothermal reforming (ATR) involves the addition of air or oxygen with relatively smaller proportions of steam to a hydrocarbon feedstock. Reaction of hydrocarbon with oxygen proceeds according to the following general reaction schemes:

$$C_nH_m + (n/2)O_2 \leftrightarrow nCO + (m/2)H_2 \quad (5)$$

and $$C_nH_m + (n + m/4)O_2 \leftrightarrow nCO_2 + m/2 H_2O \quad (6)$$

When methane is the hydrocarbon undergoing oxidative reforming, these reactions become:

$$CH_4 + \tfrac{1}{2}O_2 \leftrightarrow CO + 2H_2 \quad (7)$$

and $$CH_4 + 2O_2 \leftrightarrow CO_2 + 2H_2O \quad (8)$$

Autothermal reforming employs both steam reforming and oxidative reforming of the hydrocarbon feed. The exothermic oxidation of the feedstock hydrocarbons generates sufficient heat to drive the endothermic steam reforming reaction over the catalyst bed. The ATR procedure is thus run at relatively high temperatures and pressures with a relatively low steam to carbon ratio. The $CO_2$ content of the syngas from ATR processes, however, is fairly low, as is desirable for methanol synthesis.

Another known reforming process involves primarily partial oxidation of a hydrocarbon feed with an oxygen-containing gas. Catalytic partial oxidation reforming procedures are known; for purposes of this invention, partial oxidation reforming takes place in the absence of a catalyst. Due to the absence of a catalyst, partial oxidation (POX) reforming can operate at very high temperatures with little or no steam addition to the feedstock. Higher pressures than are used in ATR operations can be employed in POX reforming. However, the syngas composition resulting from POX reforming is generally deficient in hydrogen for methanol synthesis, resulting in $S_N$ and $H_2$:CO numbers below 2. On the other hand, the $CO_2$ content of the resulting syngas is generally very low which is below the optimum value for methanol synthesis.

It is known in the prior art to utilize various combinations of reforming operation types and procedures in the preparation of syngas mixtures which can be converted, for instance, into oxygenates. For example, Texaco's U.S. Pat. No. 5,496,859 discloses a method for the production of a "stoichiometric ratioed syngas". The method comprises partially oxidizing a gaseous feedstock containing substantial amounts of methane in a gasifier to produce a hot synthesis gas stream that is passed in indirect heat exchange through a steam reforming catalytic reactor. A portion of the steam reforming reaction products are mixed with the cooled gasifier synthesis gas stream exiting the steam reforming catalytic reactor to form a stoichiometric ratioed synthesis gas. The stoichiometric ratioed synthesis gas stream can then be passed into a methanol synthesis unit at substantially the specifications for optimal methanol production with little or no external compression. The stoichiometric ratio, $S_N$, in the syngas produced is said to range from 1.9 to 2.1. Syngas having an $S_N$ of 1.9 and an $H_2$/CO ratio of 2.52 are exemplified in the '859 patent. The exemplified syngas has an excessively high $CO_2$ content of 5.3% (on a water-free basis).

Haldor Topsoe's U.S. Pat. No. 6,224,789 and related publication [Aasberg-Petersen et al.; *Applied Catalysis, A: General* (2001), 221 (1-2), pp. 379-387] both disclose an arrangement similar to that of the Texaco '859 patent wherein effluent gas from an ATR unit circulates around and supplies heat to the HTCR (a heat exchanger version of a steam reforming reactor), but does not undergo chemical reaction there. The exemplified Haldor Topsoe process provides a syngas with a $S_N$ stoichiometric ratio of 3.66 and a $H_2$/CO ratio of 3.25.

Shell's U.S. Published Application No. 2004/0241086 discloses a process for the preparation of syngas from a gaseous hydrocarbon feedstock by (a) partial oxidation of a part of the feedstock and (b) steam reforming of another part of the feedstock. The mixture obtained in step (b) may be directly combined with the product gas as obtained in step (a). No description of feedstock or syngas composition characterized by component concentration is given.

ICI's U.S. Pat. No. 5,252,609 discloses a syngas production process involving the steam reforming and oxygen-blown reforming treatment of two separate hydrocarbon feedstock streams. Such a process comprises (a) steam reforming a first stream of desulfurized hydrocarbon feedstock, optionally, followed by secondary reforming using an oxygen-containing gas and then cooling, (b) steam reforming a second stream of the feedstock, preferably adding a hydrogen-containing gas, and then subjecting the product to partial oxidation with an oxygen-containing gas and then cooling, and (c) mixing the two cooled product streams.

Shell's WO 04/092062 and WO 04/092063 both disclose other syngas production processes involving a combination of different types of reforming operations. Such processes comprise (a) partial oxidation of a carbonaceous feedstock thereby obtaining a first gaseous mixture of hydrogen and carbon monoxide, (b) steam reforming a carbonaceous feedstock, wherein the steam to carbon molar ratio is below 1, to obtain as a steam reforming product, (c) feeding the steam reforming product to the upper end of the partial oxidation reactor to obtain a mixture of the effluent of step (a) and the steam reformer product, and (d) providing the required heat for the steam reforming reaction in step (b) by convective heat exchange between the mixture obtained in step (c) and the steam reformer reactor tubes, thereby obtaining a hydrogen and carbon monoxide containing gas having a reduced temperature.

Praxair/Standard Oil's U.S. Pat. No. 6,402,988 discloses the following: "An exothermic reaction and an endothermic reaction are thermally combined in a reactor having at least one oxygen selective ion transport membrane that provides the exothermic reaction with oxygen from an oxygen-containing gas such as air. The thermal requirements of the endothermic reaction are satisfied by the exothermic reaction. Dependent on the reactor design employed, the exothermic and endothermic reactions may be gaseously combined". The exothermic reaction is partial oxidation; the endothermic reaction is steam reforming.

Davy McKee's WO 93/15999 shows an arrangement, with steam reforming and partial oxidation (POX) units in parallel. The effluents are combined and in this arrangement are sent to a secondary reforming zone for further reduction in product methane content.

U.S. Pat. No. 5,310,506 discloses the production of synthesis gas for methanol synthesis and reacting the synthesis gas in the presence of a catalyst to produce a high-methanol product stream. Water at 1.2 to 2.0 molecules water per carbon atom in the feed gas, oxygen at 0.4 to 0.8 molecules oxygen per carbon atom in the feed gas, a high-hydrogen gas which contains free hydrocarbon at 0.2 to 0.5 molecules hydrogen per carbon atom in the feed gas, and a feed gas containing methane are fed into an ATR. The high-hydrogen gas comes at least in part from a plant other than from the instant methanol process. The reactor is operated at a pressure of 10 to 100 bars (1 to 10 MPa) and the raw synthesis gas is withdrawn at a temperature in the range of from 850° C. to 1100° C. The raw synthesis gas contains methane not in excess of 3 mol %, without removal of carbon dioxide producing a synthesis gas with a $S_N$ of from 1.97 to 2.2.

Although a variety of autothermal reforming operation systems have been proposed and methods of adjusting the $S_N$ have been proposed, additional and further efficient systems are sought that incorporate external hydrogen streams in order to adjust the $S_N$.

By adding a hydrogen stream to a reforming reactor, the temperature of the reforming reaction can be reduced, but the conversion rate is maintained and the $S_N$ is adjusted to the appropriate level. Another option is to add a hydrogen stream after the reforming reactor, which allows for greater capacity in the reformer and adjusts the $S_N$ to the appropriate level. Another option is to add hydrogen to the reforming reactor and to the synthesis gas withdrawn from the reforming reactor in order to adjust the $S_N$ to the appropriate level.

SUMMARY OF THE INVENTION

This invention provides processes for producing synthesis gases in a manner that reduces cost by efficiently utilizing hydrogen from an external process. The processes also enable the production of synthesis gases having a $S_N$ that is highly beneficial for producing oxygenated compounds, particularly alcohol products such as methanol.

According to one aspect of the invention, there is provided a process for producing synthesis gas as defined in any one of the accompanying claims. One embodiment of the present invention is a method of producing synthesis gas for methanol synthesis, said method comprising the steps of: (a) obtaining a hydrogen stream comprising greater than 5 mol % methane from a hydrocarbon conversion process; (b) feeding into a reforming reactor: (i) a feed gas comprising methane, (ii) water in a sufficient amount to have less than 1.2 moles water per mole carbon in said feed gas, (iii) oxygen in a sufficient amount to have from 0.4 to 0.8 moles oxygen per mole carbon in said feed gas, and (iv) said hydrogen stream in a sufficient amount to have from 0.01 to 0.5 moles hydrogen per mole carbon in said feed gas; (c) reacting said feed gas, water, oxygen and said hydrogen stream in said reactor at a pressure in the range of from 10-100 bars (1-10 MPa) to form said synthesis gas; and (d) withdrawing from said reactor said synthesis gas, wherein said synthesis gas: (i) is at a temperature greater than 900° C., alternatively greater than 950° C., alternatively greater than 1000° C., (ii) comprises less than 3 mol % methane, and (iii) has a stoichiometric number of from 1.9 to 2.3. Processes for obtaining a hydrogen stream comprising greater than 5 mol % methane from a hydrocarbon conversion process include, but are not limited to, steam cracking, naphtha reforming (related to gasoline production), alkane dehydrogenation (related to detergent manufacture) and propane cylclization (related to benzene production, e.g., UOP Cyclar™ process).

One embodiment of the present invention is a method of producing synthesis gas for methanol synthesis, said method comprising the steps of: (a) obtaining a hydrogen stream comprising greater than 5 mol % methane from a hydrocarbon conversion process; (b) feeding into a reforming reactor: (i) a feed gas comprising methane, (ii) water in a sufficient amount to have less than 1.2 moles water per mole carbon in said feed gas, (iii) oxygen in a sufficient amount to have from 0.4 to 0.8 moles oxygen per mole carbon in said feed gas, and (iv) said hydrogen stream in a sufficient amount to have from 0.01 to 0.5, preferably 0.05 to 0.4, more preferably from 0.1 to 0.3 moles hydrogen per mole carbon in said feed gas; (c)

reacting said feed gas, water, oxygen and said hydrogen stream in said reactor at a pressure of 10-100 bars (1-10 MPa) to form a raw synthesis gas; (d) withdrawing from said reactor said raw synthesis gas, wherein said raw synthesis gas: (i) is at a temperature greater than 1000° C. and (ii) comprises less than 3 mol % methane; and (e) adding a second portion of said hydrogen stream to said raw synthesis gas in an amount sufficient to form said synthesis gas having a stoichiometric number of from 1.9 to 2.3.

One embodiment of the present invention is a method of producing synthesis gas for methanol synthesis, said method comprising the steps of: (a) obtaining a hydrogen stream comprising greater than 5 mol % methane from a hydrocarbon conversion process; (b) feeding into a reforming reactor: (i) a feed gas comprising methane, (ii) water in a sufficient amount to have less than 1.2 moles water per mole carbon in said feed gas, and (iii) oxygen in a sufficient amount to have from 0.4 to 0.8 moles oxygen per mole carbon in said feed gas; (c) reacting said feed gas, water, and oxygen in said reactor at a pressure in the range of from 10-100 bars (1-10 MPa) to form said synthesis gas; (d) withdrawing from said reactor said synthesis gas, wherein said synthesis gas: (i) is at a temperature greater than 1000° C., and (ii) comprises less than 3 mol % methane; (e) contacting said hydrogen stream with said synthesis gas in a sufficient amount so that the stoichiometric number of said synthesis gas is from 1.9 to 2.3.

In another embodiment, in addition to the limitations above, said hydrogen stream is obtained from a hydrocarbon conversion process for thermally cracking hydrocarbons without a secondary purification step, e.g., the use of a methanation reactor, membrane separation or Pressure Swing Adsorbtion (PSA) unit. Such a hydrocarbon conversion process may be a steam cracker for ethylene production.

In another embodiment, in addition to the limitations above, said reforming reactor is an autothermal reformer. For an autothermal reformer, less than 1.0 molecule water is being fed to said reactor per carbon atom in said feed gas being fed to said reactor.

In another embodiment, in addition to the limitations above, said synthesis gas withdrawn from said reactor has a temperature greater than 1100° C., more preferably a temperature from 1100° C. to 1400° C. At such a temperature, said reforming reactor is a partial oxidation reactor. For a partial oxidation reactor, less than 0.2 molecule water is being fed to said reactor per carbon atom in said feed gas being fed to said reactor.

In another embodiment, in addition to the limitations above, said synthesis gas withdrawn from said reactor has a stoichiometric number of from 1.95 to 2.15 without removal of carbon dioxide from said synthesis gas.

In another embodiment, in addition to the limitations above, less than 0.2 molecule water is being fed to said reactor, 0.4 to 0.8 molecule oxygen is being fed to said reactor and 0.1 to 0.3 molecule hydrogen is being fed to said reactor per carbon atom in said feed gas and said hydrogen stream being fed to said reactor.

In another embodiment, in addition to the limitations above, said hydrogen stream comprises greater than 10 mol % methane.

In another embodiment, in addition to the limitations above, said hydrogen stream comprises greater than 1000 mol ppm CO.

In another embodiment, in addition to the limitations above, the present invention is a method of synthesizing methanol comprising: feeding said synthesis gas to a methanol synthesis reactor; and synthesizing said synthesis gas at a temperature and pressure effective to form methanol.

Any two or more of the above embodiments can be combined to describe additional embodiments of the invention of this patent application.

DETAILED DESCRIPTION OF THE INVENTION

I. Manufacturing Synthesis Gas

This invention is directed to a process for producing synthesis gas (or syngas) and to uses of the synthesis gas. Synthesis gas comprises carbon monoxide and hydrogen. Optionally, any one or more of carbon dioxide, water, methane and nitrogen are included. In one embodiment of the invention, the synthesis gas made according to this invention is used in the manufacture of alcohol, particularly methanol.

II. Hydrogen Stream Production

Commercial production of olefins, such as ethylene, propylene, isobutylene, butadiene, normal butylenes, and others, is commonly achieved through the pyrolysis of hydrocarbon feedstocks. Steam is typically added to the feed to reduce the yield of byproducts such as coke, and therefore such processes are commonly referred to as steam cracking. The feedstocks can be ethane, propane, naphthas, gas oils, isobutane, and in general, any hydrocarbon stream containing paraffinic molecules with 2 or more carbon atoms. Aside from olefins, the products from steam cracking include hydrogen, methane, CO, and coke. In the purification of the olefin products, a cyrogenic flash or distillation step to separate hydrogen from methane and ethylene is typically employed, and is commonly referred to as a cold box. The cold box, cryogenic purification step comprises a series of heat exchangers, separator drums, and flash steps to effect the separation of hydrogen from methane and higher boiling point components. In a simple cold box flash or distillation scheme, the hydrogen and some higher boiling point components are withdrawn in the overhead product, and the methane and ethylene and heavier components are withdrawn as bottoms products. The overhead stream comprises the hydrogen, and some methane, CO, ethylene and potentially trace amounts of oxygen, ethane, propane and nitrogen as well. In a typical steam cracking process, the hydrogen content of this stream is 70 mol % or higher, with 2000-3000 ppm of CO, with the balance comprising generally inert methane. It is common to purify the hydrogen stream to reduce the concentration of other components, because hydrogen is a more valuable byproduct if it is high purity, greater than 90 mol %. Also, for many processes that use hydrogen, including some catalytic hydrogenation reactions, such contaminants as CO and olefins may be very detrimental to the catalyst and process performance.

Similarly, other well known hydrocarbon conversion processes produce significant quantities of hydrogen with significant quantities of inerts or contaminants. These include, but are not limited to, naphtha reforming for motor gasoline production, alkane dehydrogenation for detergent manufacture and propane cylclization to benzene (e.g., UOP Cyclar™ process), among others. In these processes, which tend to produce products of significantly higher boiling points than ethylene, cryogenic operations may not be required as the base hydrogen separation scheme, but rather straightforward higher temperature distillation or flashes suffice.

In one secondary purification method, membranes may be used to concentrate hydrogen in the permeate stream and concentrate methane in the retentate stream. The concentrated hydrogen stream leaves at a much reduced pressure, and generally requires a compressor to boost the pressure back to a useful level. In yet another secondary purification method, a solid adsorbent may be used to adsorb methane and other impurities from the hydrogen stream, increasing the hydrogen purity of the adsorber effluent. In this method, the adsorbent must be periodically regenerated, either by heating, lowering the pressure, or a combination of both. Multiple adsorbent beds and switching valves must be used in this method to allow for the continuous production of the concentrated hydrogen stream. None of the above methods are effective at totally eliminating the CO content of the hydrogen stream; if zero CO is required, then a methanation reaction step is added to convert CO to $CH_4$ and $H_2O$ via hydrogenation. The methanation reaction will also generally fully hydrogenate any unsaturates in the hydrogen bearing stream, such as olefins, rendering them basically inert.

It would be desirable to utilize the total hydrogen bearing stream from a simple base recovery scheme, such as a cryogenic cold box on a steam cracker, where the full value of the hydrogen is realized without having to add expensive reaction, membrane, or adsorption hydrogen concentration or contaminant removal steps. The present invention utilizes said hydrogen in one of several ways to correct the stoichiometry of the syngas, while still maintaining a crude methanol product with low water content.

In one embodiment, the hydrogen stream comprises greater than 5 mol % methane, or greater than 7 mol % methane, or greater than 9 mol % methane, or greater than 10 mol % methane. The hydrogen stream comprises greater than 100 mol ppm CO, 500 mol ppm CO, 1000 mol ppm CO, 2000 mol ppm CO, or 5000 mol ppm CO. The hydrogen stream comprises no greater than 95 mol % hydrogen, or no greater than 92 mol % hydrogen, or no greater than 90 mol % hydrogen, or no greater than 85 mol % hydrogen. The hydrogen stream comprises greater than 100 mol ppm olefins, 500 mol ppm olefins, 1000 mol ppm olefins, 2000 mol ppm olefins, or 5000 mol ppm olefins. Exemplary olefins include ethylene, or propylene, or a combination thereof.

The hydrogen stream may be obtained from any hydrocarbon conversion process including, but not limited to, steam cracking, e.g., for ethylene production, and other dehydrogenation processes, e.g., naphtha reforming for motor gasoline production, alkane dehydrogenation for detergent manufacture and propane cylclization to benzene (UOP Cyclar™ process), among others. The hydrogen stream may be obtained from a hydrocarbon process without a secondary purification step, e.g., the use of a methanation reactor, membrane separation or Pressure Swing Adsorbtion (PSA) unit. The use of such a secondary purification step would increase the hydrogen purity of said hydrogen stream obtained from the base recovery system, for example, by a cryogenic flash or distillation step in a steam cracker, or higher temperature flash or distillation in a naphtha reforming facility. Therefore the exclusion of such step allows for an increase in the methane and other components present in the hydrogen stream at a reduced investment (due to the avoidance of the secondary purification step).

III. Synthesis Gas Production

Synthesis gas can be manufactured from a variety of carbon sources, although the main interest of the present invention is with natural gas feedstocks comprising methane. The reforming of hydrocarbons into syngas is an endothermic reaction, and heat must be supplied to make the reaction proceed. There are generally two methods of adding heat: (i) indirect heating, generally by burning a fuel and transferring this heat across a metal membrane to the reaction zone, and (ii) in-situ heat generation by adding oxygen to the reformer feed, which results in exothermic oxidation reactions which may supply heat for the endothermic reaction. Steam is necessary in method (i), and is often called steam reforming. In method (ii), oxygen is always added, and will be referred to as "oxygen-blown" reforming. Various combinations of (i) and (ii) are possible, and will be referred to as "combined reforming".

Oxygen blown reforming may be operated with or without a catalyst. When no catalyst is used, the process will be referred to as Partial Oxidation, or POX. The feedstock hydrocarbon and oxygen-containing gas are preheated and react in a burner. When catalyst is used, the oxygen-blown reforming may be further subdivided into two categories. If the feedstock hydrocarbon and oxygen-containing gas are pre-mixed, without reaction, before passing across a catalyst bed, the process will be referred to as Catalytic Partial Oxidation, or CPOX. When preheated feedstock and oxygen are combined in a burner, where exothermic reactions occur, before passing across a catalyst bed, the process will be referred to as Autothermal Reforming, or ATR. The POX or CPOX processes are net exothermic processes, although some of the heat of combustion will be used in endothermic reforming reactions that take place at elevated temperatures even in the absence of a catalyst. The ATR process is approximately thermoneutral, with the heat release of combustion about offsetting the heat consumed by the catalytic portion of the reactor.

Steam reformers operated with natural gas feedstock produce syngas that is rich in hydrogen, with stoichiometric numbers ($S_N$) approaching 3.0. Oxygen-blown reformers produce syngas that is less rich in hydrogen, and generally have $S_N$ values below the theoretical required value for methanol of 2.0. The present invention is directed at reforming processes that naturally produce sub-stoichiometric syngas, which includes any of the oxygen-blown reforming processes.

The amount of oxygen added to an oxygen-blown reformer depends upon the pressure, feed temperatures, feed compositions and diluent rates, and the desired level of conversion. The total molar flow rate of oxygen added to the reformer, divided by the flow rate of hydrocarbon-based carbon atoms fed to the reformer, will be referred to as the oxygen:carbon ratio.

Steam may be added to an oxygen-blown reformer, either as diluent to the hydrocarbon feedstock, diluent to the oxygen-containing gas, or may be directly injected into a specific portion of the reforming reactor to achieve localized cooling. The total molar flow rate of steam added to the oxygen-blown reformer in any manner, divided by the flow rate of hydrocarbon-based carbon atoms fed to the reformer, will be referred to as the steam:carbon ratio.

In the autothermal reforming of natural gas, steam is added to the feed as a means to reduce or eliminate soot formation, to cool select components of the burner within the ATR, and to reduce the methane content of the syngas at a given temperature. It is desirable to minimize the amount of steam added, so that less energy is required for generation of the steam, and so that the volume of gas passing through the reformer is minimized. ATR reactors generally require steam:carbon ratios of 1.2 to 2.0, although more recent technology allows operation in the 0.4 to 1.2 range. The oxygen:carbon ratio of an ATR ranges between 0.4 to 0.8, preferably between 0.5 and 0.7.

In the partial oxidation of natural gas, the formation of soot is less of a concern because there is no catalyst bed to become fouled or plugged by the soot. Therefore, POX reformers can run with very little or no steam, with steam:carbon ratios between 0 and 0.2. The oxygen:carbon ratio of POX reformers ranges between 0.4 to 0.8, preferably between 0.55 and 0.7.

The catalytic partial oxidation reforming process has not been commercialized to-date for methanol synthesis applications. A CPOX reforming process can theoretically operate with steam:carbon ratios below 0.2, or at any higher level of steam:carbon. A CPOX reformer will generally operate with an oxygen:carbon ratio between 0.4 and 0.8.

Any oxygen-blown reforming reactor will generally reach a product gas that approaches the most thermodynamically stable composition. One skilled in the art can calculate the adiabatic temperature and product syngas composition at thermodynamic equilibrium for any given feed composition, feed temperature, and pressure. The relative amounts of CO and $CO_2$ in the syngas is determined by the water gas shift (WGS) reaction equilibrium represented in equation (3) above.

Increasing the level of steam added to the reformer will shift the reaction to the right, resulting in a greater proportion of $CO_2$ relative to CO. Higher reaction temperatures shift the equilibrium of the WGS to the left, resulting in reduced proportions of $CO_2$ relative to CO. It is easily shown that the stoichiometric number for methanol, $S_N$, is not affected by shifting between CO and $CO_2$ due to the WGS reaction. The $CO_2$ content of the syngas, however, is affected by the WGS reaction. Low levels of $CO_2$ in the syngas are favored by low steam:carbon and high temperatures in the reformer.

In reforming processes of the present invention that use a catalyst, the catalyst comprises at least one transition element selected from the group consisting of Ni, Co, Pd, Ru, Rh, Ir, Pt, Os, and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the reforming catalyst further comprises at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, optionally, included in the partial oxidation catalyst is at least one rare earth element selected from the group consisting of La, Ce, Pr, Nd, Pm, Sm, Eu, Gd, Tb, Dy, Ho, Er, Tm, Yb, and Lu.

In another embodiment the reforming catalyst employed in the process may comprise a wide range of catalytically active components, for example, Pd, Pt, Rh, Ir, Os, Ru, Ni, Cr, Co, Ce, La, and mixtures thereof. Materials not normally considered to be catalytically active may also be employed as catalysts, for example, refractory oxides such as cordierite, mullite, mullite aluminum titanate, zirconia spinels, and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the reforming catalyst comprises at least one transition or non-transition metal deposited on a monolith support. The monolith supports are preferably impregnated with a noble metal such as Pt, Pd or Rh, or other transition metals such as Ni, Co, Cr, and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

The reforming process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars (15 MPa). Preferably, the partial oxidation process is operated at a pressure in the range of from about 2 bars (200 kPa) to about 125 bars (12.5 MPa), more preferably from about 5 bars (500 MPa) to about 100 bars (10 MPa).

The reforming process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1700° C., more preferably from about 800° C. to about 1600° C. The feed mixture is preferably preheated prior to contacting the catalyst.

IV. Making Methanol with Synthesis Gas

Methanol can be produced from the reaction of hydrogen with either CO or $CO_2$. Two molecules of hydrogen react with one of CO to form one molecule of methanol. Three hydrogen molecules must react with $CO_2$ to form one methanol molecule, with the generation of one molecule of byproduct water.

While the byproduct water can be distilled from the product methanol, such a distillation process requires the addition of energy and equipment. It would be desirable to save the energy and equipment cost by eliminating the separation of water and methanol. The elimination of the water/methanol separation is enabled if the crude methanol produced has an inherently low water content. Crude methanol with low water content is produced if the amount of $CO_2$ in the syngas feedstock is minimized. As previously described, the $CO_2$ content is minimized by operating the reforming conditions with low steam:carbon and high reformer exit temperature. Therefore, the production of crude methanol with low water content is enabled by a reforming technology choice that utilizes high reforming exit temperatures and low steam:carbon ratios. It is desirable to operate with a reforming exit temperature greater than 1000° C., preferably greater than 1100° C., and with a steam:carbon ratio less than 1.2, preferably less than 0.8, in order to reduce the $CO_2$ content of the syngas to less than about 4 mol % (dry basis).

The present invention is particularly useful for correcting the stochiometry of syngas produced from a reforming process with exit temperatures greater than 1000° C., preferably greater than 1100° C., and with a steam:carbon ratio less than 1.2, preferably less than 0.8. Such reforming conditions are feasible only through oxygen-blown reforming processes. The application of oxygen-blown reforming operating at high temperature and low steam:carbon results in a syngas stoichiometry that is deficient in hydrogen for methanol production. In the present invention, the syngas stoichiometry is corrected by combining a hydrogen-rich stream from an external process, for example, the pyrolysis of hydrocarbons for olefin manufacture.

The synthesis gas made according to this invention is preferably sent to an oxygenate synthesis process (i.e., a carbon oxide conversion process) and converted to an oxygenate composition. Preferably, the synthesis gas is sent to a methanol synthesis process for converting into a methanol composition, which optionally, includes other oxygenates. The methanol synthesis process is accomplished in the presence of a methanol synthesis catalyst.

In one embodiment, the synthesis gas is sent "as is" to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$–$CO_2$) to carbon oxides ($CO+CO_2$), or $S_N$, in the range of from about 0.5 to about 5, preferably in the range of from about 1.5 to about 3.0, more preferably from about 1.9 to about 2.3, more preferably from about 1.95 to about 2.2, and most preferably from about 2.0 to about 2.15. In another embodiment, the synthesis gas has a molar ratio of hydrogen ($H_2$) to carbon monoxide (CO) of at least 2:1. Carbon dioxide is, optionally, present in an amount of not greater than 50% by weight, based on total weight of the synthesis gas.

The $CO_2$ content, relative to that of CO, in the synthesis gas should be high enough so as to maintain an appropriately high reaction rate and to minimize the amount of undesirable by-products such as paraffins. At the same time, the relative $CO_2$ to CO content should not be too high so as to reduce methanol yield and generate byproduct water. Conveniently, the synthesis gas contains a ratio of $CO_2$ to CO of from about 0.05 to about 1.0, preferably from about 0.1 to about 0.5.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium, and zirconium. Preferably, the catalyst is a copper-based catalyst, more preferably in the form of copper oxide.

In another embodiment, the catalyst used in the methanol synthesis process is a copper-based catalyst, which includes an oxide of at least one element selected from the group consisting of silver, zinc, boron, magnesium, aluminum, vanadium, chromium, manganese, gallium, palladium, osmium, and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis catalyst contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

$$CO+2H_2 \rightarrow CH_3OH \qquad (10)$$

$$CO_2+3H_2 \rightarrow CH_3OH+H_2O \qquad (11)$$

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities can vary as desired. Preferably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

In one embodiment of the invention, crude methanol is produced from the methanol synthesis process. The crude methanol is then processed to form a methanol feed. Preferably, the methanol feed is of sufficiently high quality to use a feed in a catalytic methanol conversion reaction to form light olefins, particularly substantial amounts of ethylene and propylene, for example, by conversion of the crude methanol in a reaction over a silicoaluminophosphate catalyst. Such light olefins can be subsequently sent to a polymerization reactor and subjected to well known process conditions to form a variety of polyolefins. Polyolefins include polymers which comprise the reaction product of one or more light olefins. Such polymers include homopolymers and copolymers of one or more light olefins, including copolymers with monomers from other sources. Such monomers from other sources can be either polar or nonpolar. The crude methanol may contain from 0.2 to 25.0 wt. % water, or 0.5 to 20.0 wt. % water, or 1.0 to 15.0 wt. % water, or 2.0 to 10.0 wt. % water. The crude methanol may contain from 0.01 to 25.0 wt. % ethanol, or 0.02 to 20.0 wt. % ethanol, or 0.03 to 15.0 wt. % ethanol. The crude methanol may comprise from 1 to 5000 wppm, or 2 to 2000 wppm, or 5 to 1000 wppm of one or any combination of C3+ alcohols, aldehydes, ketones, ethers, carboxylic acids, or aliphatic hydrocarbons.

Processing of the crude methanol can be accomplished using numerous means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol and desirable aldehydes and/or other desirable alcohols also present.

In one embodiment, the crude methanol product from the methanol synthesis reactor is further treated to reduce water content and other undesirable impurities prior to converting to olefin product. Conventional treatment processes can be used. Examples of such processes include distillation, selective condensation, and selective adsorption.

In one embodiment, a crude methanol stream comprising methanol, dimethyl ether, fusel oils (i.e., hydrocarbons and oxygenates having a boiling point greater than methanol), and water is withdrawn from a carbon oxide conversion zone. The crude methanol stream is then passed to a distillation column, conventionally referred to as a topping column. Desirably, the topping column operates at a pressure of from about 20 kPa to about 200 kPa. Preferably, the topping column operates at a pressure of from about 25 kPa to about 150 kPa, more preferably from about 30 kPa to about 125 kPa, and most preferably from about 40 kPa to about 100 kPa.

A first light ends stream is removed from an upper portion of the topping column. Preferably, the light ends stream contains dissolved gases (e.g., hydrogen, methane, carbon oxides, and nitrogen), and light ends (e.g., ethers, ketones, and aldehydes). In one embodiment of the invention, the dissolved gases, the light ends, or both are used as fuel. In another embodiment, the dissolved gases, light ends, or both are sent to a synthesis gas production zone to produce additional synthesis gas, which can ultimately be converted to additional methanol, preferably further converted to olefin(s).

A bottoms stream is preferably removed from a lower portion of the topping column, and passed to a second distillation column, conventionally referred to as a refining column. From the refining column, a second light ends stream is withdrawn, preferably at an upper portion of the refining column. In one embodiment, the second light ends stream is combined with the first light ends stream from the topping column to form a combined purge stream. The combined purge stream is preferably used for fuel.

The refining column operates at a pressure of from about 0.5 atm to about 10 atm. Preferably, the refining column operates at a pressure of from about 0.6 to about 5 atm, more preferably from about 0.7 to about 3 atm, and most preferably from about 0.7 to about 2 atm. The refining column is used to further separate methanol from water and fusel oils, which remain in the bottoms stream of the topping column, so as to provide a high purity methanol stream, a fusel oil stream, and a water stream.

The methanol stream separated from the refining column is suitable for use in any system that uses methanol as a feedstream. Preferably, the methanol is suitable for use in an oxygenate conversion system.

In one embodiment, the methanol stream separated from the refining column comprises at least 98 wt % methanol, based on total weight of the methanol stream. Preferably, the methanol stream comprises at least 98.5 wt % methanol, more preferably at least 99.0 wt % methanol, and most preferably at least 99.5 wt % methanol, based on total weight of the methanol stream.

In another embodiment, the methanol stream separated from the refining column comprises less than 0.2 wt % water, based on total weight of the methanol stream. Preferably, the methanol stream comprises less than 0.15 wt % water, more preferably less than 0.1 wt % water, and most preferably less than 0.05 wt % water, based on total weight of the methanol stream.

In yet another embodiment, the methanol stream separated from the refining column comprises less than 40 wppm acetone, based on total weight of the methanol stream. Preferably the methanol stream separated from the refining column comprises less than 30 wppm acetone, more preferably less than 25 wt % acetone, and most preferably less than 20 wt % acetone, based on total weight of the methanol stream.

V. Oxygenates-to-Olefins Process

As indicated, one embodiment of the present invention provides for combining a methanol synthesis system with an oxygenates-to-olefins (OTO) reaction process. In an OTO process, typically an oxygenated feedstock, most preferably a methanol-containing feedstock, is converted in the presence of a molecular sieve catalyst composition into one or more olefins, preferably and predominantly, ethylene and/or propylene, referred to herein as light olefins.

Typically, molecular sieve catalysts have been used to convert oxygenate compounds to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

In a preferred embodiment of an integrated process of this invention, the feedstock contains one or more oxygenates in addition to methanol or, more specifically, one or more organic compounds containing at least one oxygen atom. In the most preferred embodiment of the process of the invention, the oxygenates in the feedstock (in addition to methanol) comprise one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates, in addition to methanol include ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises methanol, and one or more of DME, diethyl ether, or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1, and isomers thereof. Other olefin monomers include unsaturated monomers, diolefins having 4 to 18 carbon atoms, conjugated or nonconjugated dienes, polyenes, vinyl monomers, and cyclic olefins.

The process for converting a feedstock containing one or more oxygenates, in the presence of a molecular sieve catalyst composition, is carried out in a reaction process in a reactor, where the process is a fixed-bed process, a fluidized-bed process (includes a turbulent bed process), preferably a continuous fluidized-bed process, and most preferably a continuous high velocity fluidized-bed process.

The conversion temperature employed in the OTO conversion process, within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.), most preferably from about 662° F. (350° C.) to about 1022° F. (550° C.).

The conversion pressure employed in the OTO conversion process, within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in an OTO process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is typically maintained at a level sufficient to keep the catalyst composition in a fluidized state within a reactor.

Typically, the WHSV ranges for OTO processes from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol, DME, or both, is in the range of from about 20 hr$^{-1}$ to about 300 hr$^{-1}$.

VI. Examples of Synthesis Gas Reaction Systems

A series of examples are described below based on computer simulations of the reforming and methanol synthesis processes. In each case, the natural gas composition was kept constant. The reforming conditions were also kept constant (oxygen:carbon, steam:carbon, and feed preheat temperature). The natural gas in these examples comprised 89.75 mol % methane, 5.46 mol % ethane, and 4.80 mol % nitrogen. In the methanol synthesis reaction, unreacted syngas was recycled to the synthesis reactor feed at a rate of 14,600 kmol/h. All unreacted syngas in excess of this rate was purged (referred to as purge gas).

The composition of the steam cracker (import) hydrogen stream is 80 mol % hydrogen and 20 mol % methane. It was recognized that this stream will also include small quantities of CO in an actual case. The CO does not introduce any problems to either the reforming or synthesis reactors, so the small quantity was ignored for purposes of the calculations in these examples.

Example 1 (COMPARATIVE EXAMPLE)

This example was a base case ATR reformer operated without any means of correcting the stoichiometry of the syngas for methanol synthesis. The reforming conditions were as follows.

TABLE 1

Example 1 Process Conditions

| | |
|---|---|
| Natural gas feed rate | 3150 kmol/h |
| Steam:carbon ratio | 0.6 |
| Oxygen:carbon ratio | 0.515 |
| Reformer exit pressure | 43 bara (4.3 MPa atm.) |

In this example the ATR exit temperature was 1055° C., and the syngas had a $S_N$ value of 1.84 and a $CO_2$ content of 4.0 mol % on a dry basis. The syngas was fed to the methanol synthesis loop, where the makeup gas and recycle gas combine to produce a feed composition to the synthesis reactor with a $S_N$ value of 1.49. After stripping dissolved gases from the liquid product, the crude methanol stream had a water content of 3.2 wt %. The methanol production rate was 2025 metric tons per day.

This example showed the effect of feeding a syngas to a methanol loop that had a $S_N$ value below the theoretical value of 2.0. The effect of recycling unreacted syngas to the reactor was to further reduce the $S_N$ value. While the makeup gas had a $S_N$ value of 1.84, the $S_N$ value in the synthesis reactor feed was 1.49. This value is considered unacceptable for commercial $CuO/ZnO/Al_2O_3$ methanol synthesis catalyst systems, as the reactivity of the gas is too low and the deactivation rate of the catalyst is too high when the reaction conditions have this substoichiometric level of hydrogen.

Figure 1:
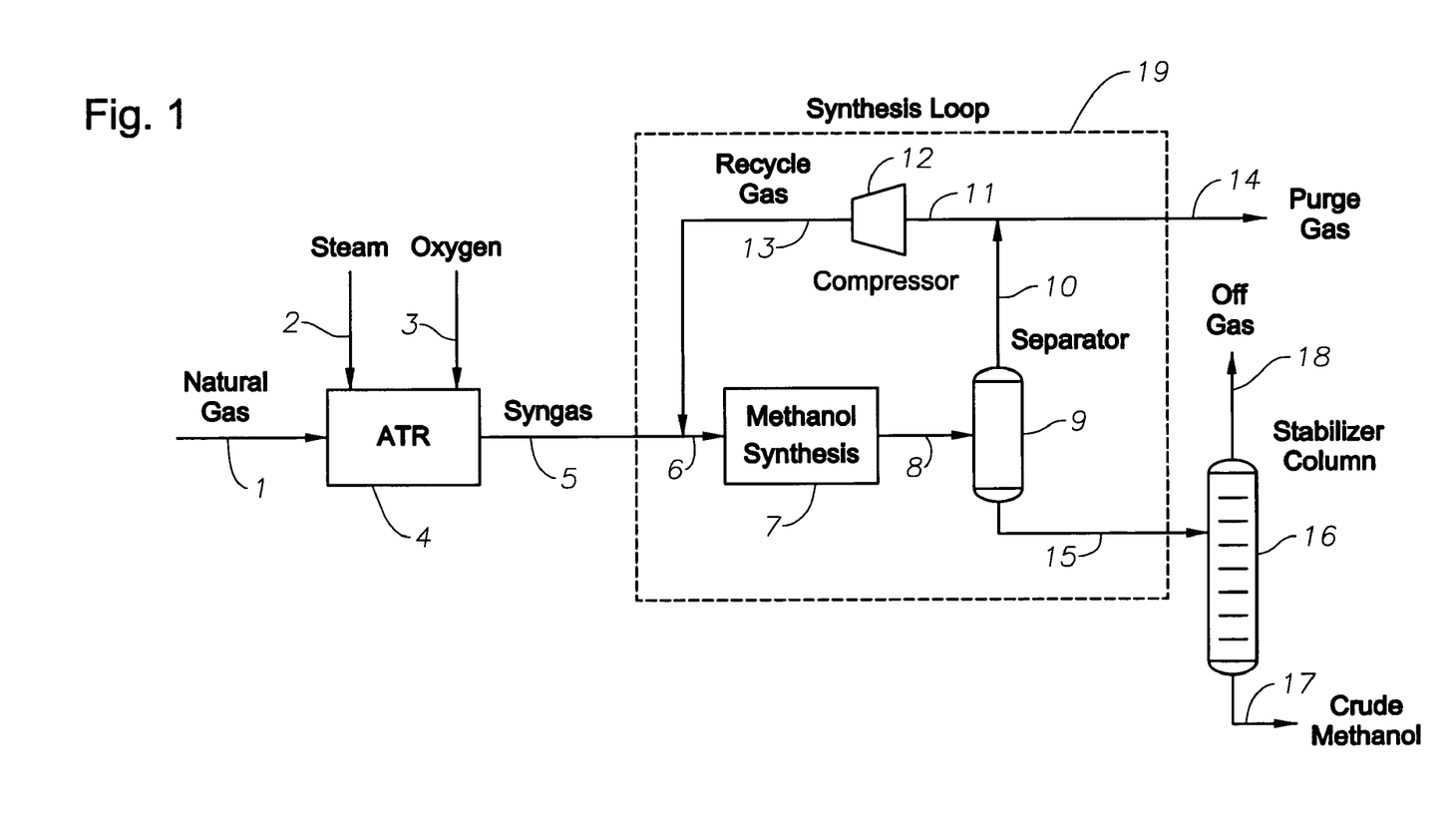
FIG. 1 shows a comparative example of a reaction system.

This example is demonstrated in FIG. 1. The natural gas stream 1, the steam stream 2, the oxygen stream 3, are fed into the reforming reactor 4, in this example an ATR. The syngas stream 5 and the recycle gas stream 13 are fed into the methanol synthesis reactor 7 via stream 6. The methanol product stream 8 is fed into a separator 9. The bottoms stream 15 is fed into a stabilizer column 16. The off-gas stream 18 is purged from the stabilizer column 16 and the crude methanol stream 17 is removed from the bottom of the stabilizer column 16. The tops stream 10 from the separator 9 is split into a purge gas stream 14 and a second stream 11, which is fed into a compressor 12, which forms the recycle gas stream 13. The synthesis loop 19 comprises the methanol synthesis reactor 7, the separator 9, the compressor 12, and all related streams as shown in FIG. 1.

Example 2 (COMPARATIVE EXAMPLE)

In this example, the ATR feed rate and conditions were identical to Example 1. The hydrogen stoichiometry was corrected by means of a device on the methanol synthesis loop that concentrated hydrogen in the syngas stream that was recycled to the reactor. The device in this example achieved recoveries of the main syngas components as follows.

TABLE 2

Example 2 recovery percentages of the main gas components

| | |
|---|---|
| Nitrogen | 91.1% |
| CO | 54.6% |
| $CO_2$ | 65.2% |
| $CH_4$ | 89.9% |
| Hydrogen | 97.5% |

The hydrogen recovery was higher than the other components, resulting in an increase in the $S_N$ value of the methanol synthesis reactor feed, from 1.49 in Example 1 to 4.67 in the present example. There was a slight loss in methanol production rate, from 2025 to 1921 metric tons per day. The water content of the crude methanol product was an acceptably low value of 4.5 wt %.

While this example provided a syngas composition to the synthesis reactor that was desirably rich in hydrogen, it required the addition of costly and complicated equipment to concentrate hydrogen from the other components in the syngas recycle loop.

Figure 2:
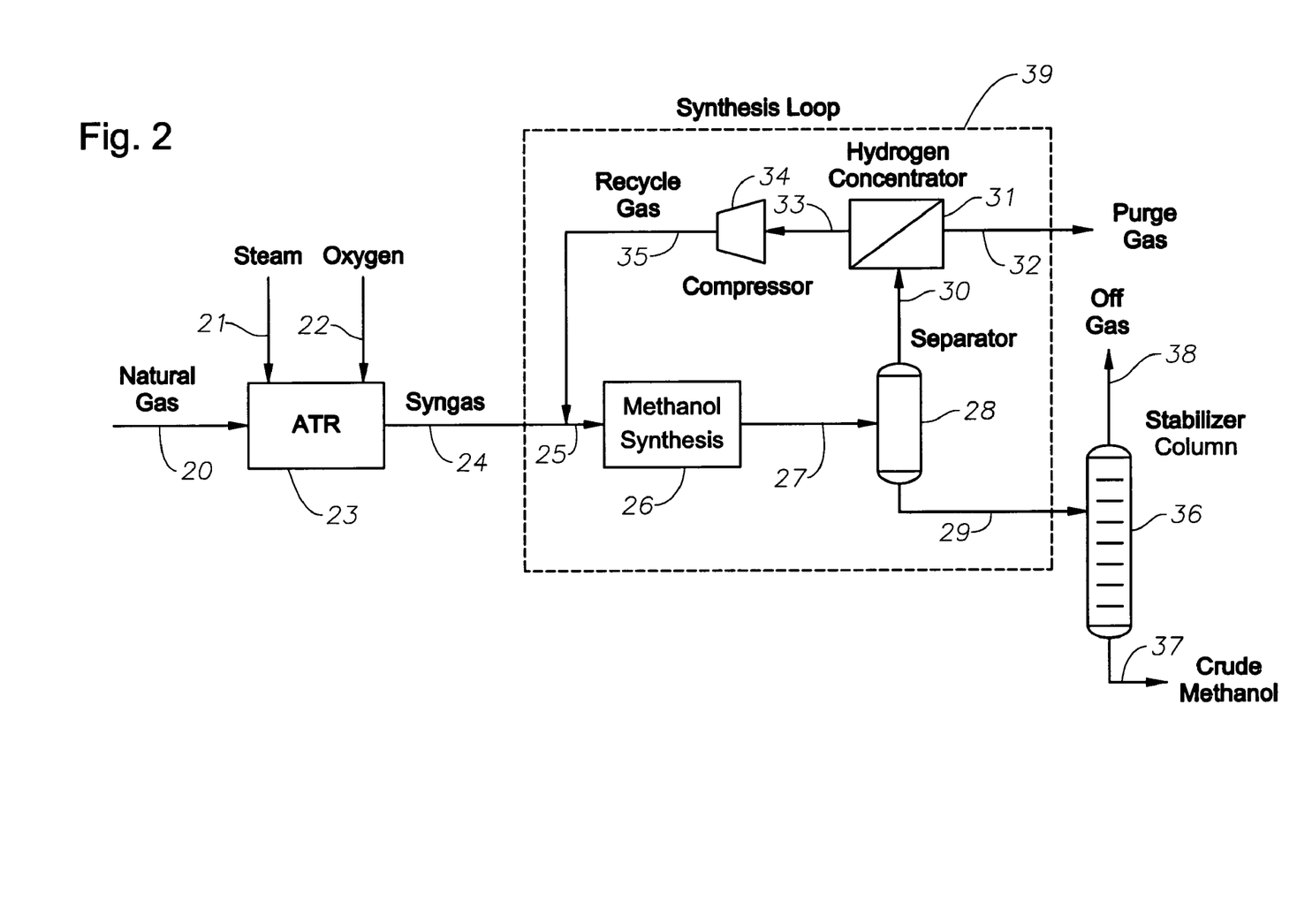
FIG. 2 shows a comparative example of a reaction system containing a hydrogen concentrator.

This example is demonstrated in FIG. 2. The natural gas stream 20, the steam stream 21, and the oxygen stream 22, are fed into the reforming reactor 23, which, in this example, is an ATR. The syngas stream 24 and the recycle gas stream 35 are fed into the methanol synthesis reactor 26 via stream 25. The methanol product stream 27 is fed into a separator 28. The bottoms stream 29 is fed into a stabilizer column 36. The off-gas stream 38 is purged from the stabilizer column 36 and the crude methanol stream 37 is removed from the bottom of the stabilizer column 36. The tops stream 30 from the separator 28 is fed into a hydrogen concentrator 31. A purge gas stream 32 is removed from the hydrogen concentrator 31. The hydrogen concentrated stream 33 is fed into a compressor 34 and the recycle gas stream 35 is compressed by the compressor 34. The synthesis loop 39 comprises the methanol synthesis reactor 26, the separator 28, the compressor 34, the hydrogen concentrator 31 and all related streams as shown in FIG. 2.

Example 3

In this example, the ATR was operated in an identical fashion to that of Examples 1 and 2. The syngas product from the ATR was mixed with the import hydrogen stream from the steam cracker (80 mol % $H_2$, 20 mol % methane), at a rate of 713 kmol/h. The stoichiometric number, $S_N$, of the syngas feed to the synthesis loop was increased from 1.84 to 2.03, bringing the hydrogen content just above the stoichiometric requirement. The $S_N$ value in the synthesis reactor feed was 2.77, which was sufficiently rich in hydrogen for good synthesis reactor operation. The methanol production rate was 2095 metric tons per day, which was an improvement over either Examples 1 or 2. The water content in the crude methanol was an acceptably low value of 4.5 wt %.

Figure 3:
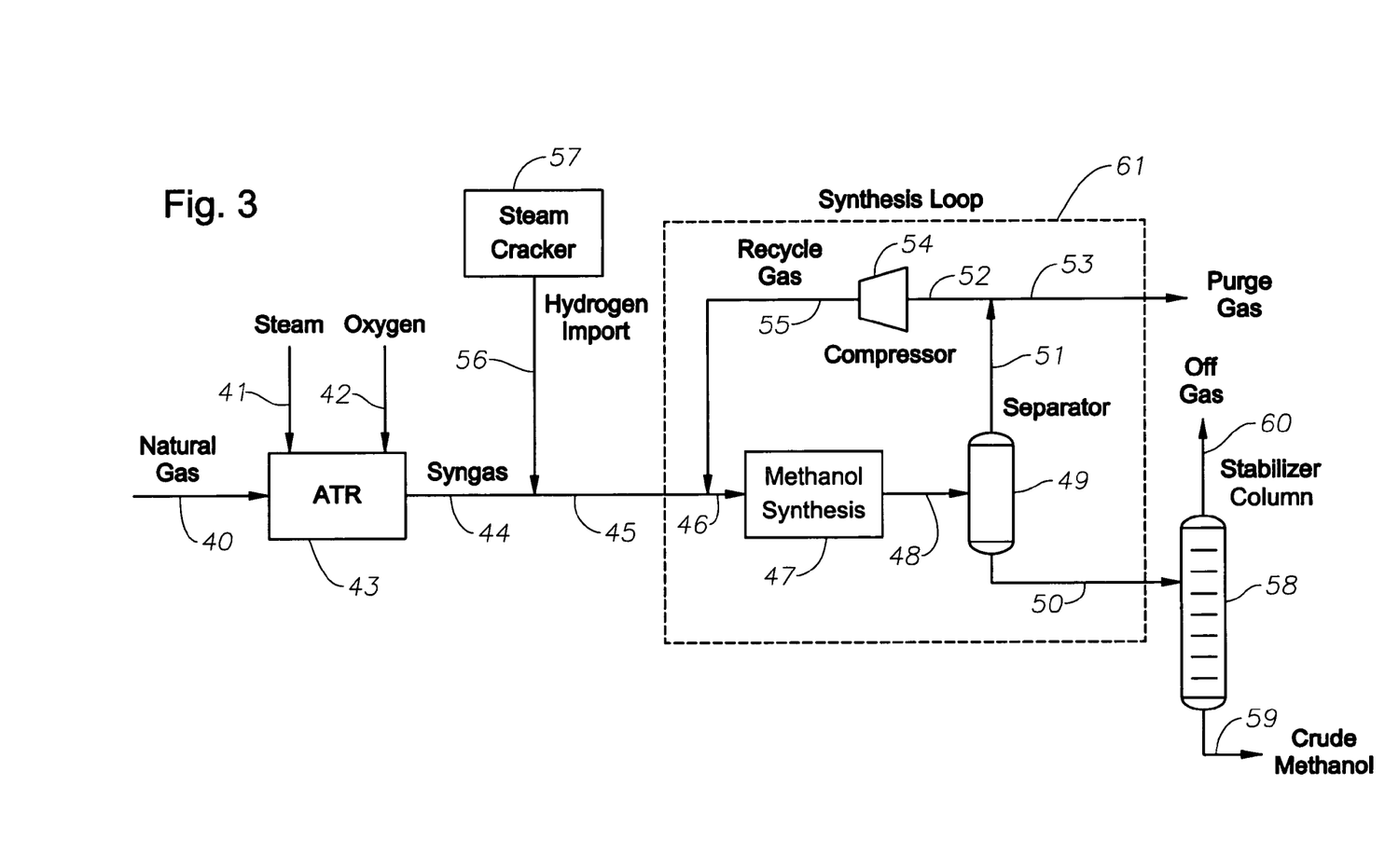
FIG. 3 shows one embodiment of the present invention wherein the hydrogen stream is derived from an external hydrocarbon conversion process and is fed to the synthesis gas stream after the reforming reactor.

This example is demonstrated in FIG. 3. The natural gas stream 40, the steam stream 41, the oxygen stream 42, are fed into the reforming reactor 43, in this example an ATR. The syngas stream 44 exits the reforming reactor 43 and a hydrogen import stream 56 from a steam cracker 57 are combined to form steam 45. A recycle gas stream 55 merges with stream 45 and both are fed via stream 44 to the methanol synthesis reactor 47. The methanol product stream 48 is fed into a separator 49. The bottoms stream 50 is fed into a stabilizer column 58. The off-gas stream 60 is purged from the stabilizer column 58 and the crude methanol stream 59 is removed from the bottom of the stabilizer column 58. The tops stream 51 from the separator 49 is split into a purge gas stream 53 and a second stream 52, which is fed into a compressor 54, which forms the recycle gas stream 55. The synthesis loop 61 comprises the methanol synthesis reactor 47, the separator 49, the compressor 54, and all related streams as shown in FIG. 3.

Example 4

In this example, the import hydrogen stream (713 kmol/h, 80 mol % $H_2$), was mixed with the natural gas feed to the ATR. The import hydrogen contained 142 kmol/h of methane, so the natural gas feed rate was reduced from 3150 to 3008 kmol/h to keep the feed rate of carbon atoms to the ATR the same as in Examples 1-3. The feed preheat temperatures, oxygen:carbon and steam:carbon ratios were identical to Examples 1-3.

As shown in Table 3, the ATR exit temperature was reduced from 1055 to 965° C., while the hydrocarbon conversion increased from 92.9 to 97.3%, compared with Examples 1-3. The $S_N$ value of the ATR syngas was 2.07. This value was above the stoichiometric requirement for methanol, and resulted in a synthesis reactor feed $S_N$ value of 3.67. The crude methanol had an acceptably low water content of 5.4 wt %. The methanol production rate was 2274 metric tons per day, representing an improvement over each of the Examples 1-3.

TABLE 3

Simulation results for Examples 1-4.

| | Example Number | | | |
|---|---|---|---|---|
| | 1 | 2 | 3 | 4 |
| Natural gas feed to ATR, kmol/h | 3150 | 3150 | 3150 | 3008 |
| Import $H_2$-rich feed to ATR, kmol/h | 0 | 0 | 0 | 713 |
| Import $H_2$-rich feed to synthesis loop, kmol/h | 0 | 0 | 713 | 0 |
| ATR exit temperature, ° C. | 1055 | 1055 | 1055 | 965 |
| Hydrocarbon conversion % | 92.9 | 92.9 | 92.9 | 97.3 |
| Syngas composition (makeup gas), mol % | | | | |
| CO | 28.3 | 28.3 | 28.3 | 26.8 |
| $CO_2$ | 4.0 | 4.0 | 4.0 | 3.7 |
| $H_2$ | 63.2 | 63.2 | 63.2 | 66.8 |

TABLE 3-continued

Simulation results for Examples 1-4.

| | Example Number | | | |
|---|---|---|---|---|
| | 1 | 2 | 3 | 4 |
| CH$_4$ | 2.5 | 2.5 | 2.5 | 0.8 |
| Makeup gas stoichiometric number, S$_N$, before H$_2$ import | 1.84 | 1.84 | 1.84 | 2.07 |
| Makeup gas stoichiometric number, S$_N$, after H$_2$ import | 1.84 | 1.84 | 2.03 | 2.07 |
| Synthesis reactor feed stoichiometric number | 1.49 | 4.67 | 2.77 | 3.67 |
| Methanol product MT/d | 2025 | 1921 | 2095 | 2274 |
| Crude methanol water wt % | 3.2 | 4.5 | 4.5 | 5.4 |

While the use of import hydrogen from a steam cracker can be used advantageously as a feed to the methanol synthesis loop, as shown in Example 3, the present example demonstrated the following additional advantages: a reduction in the ATR exit temperature from 1055 to 965° C., which resulted in improved life of the ATR reactor components due to less severe temperature conditions; an increase in the hydrocarbon conversion across the ATR, from 92.9 to 97.3% which resulted in a reduction in the methane content of the syngas from 2.5 to 0.8%, which reduced the accumulation of methane in the synthesis recycle loop; the reduction in methane content in the syngas feed to the synthesis loop improves carbon utilization, resulting in an increase in the methanol production rate from 2095 to 2274 metric tons per day, using the same feed rate of carbon atoms to the ATR reactor; the increased methanol production in Example 4 was achieved using less natural gas feed, 3008 kmol/h compared with 3150 kmol/h in Example 3.

Figure 4:
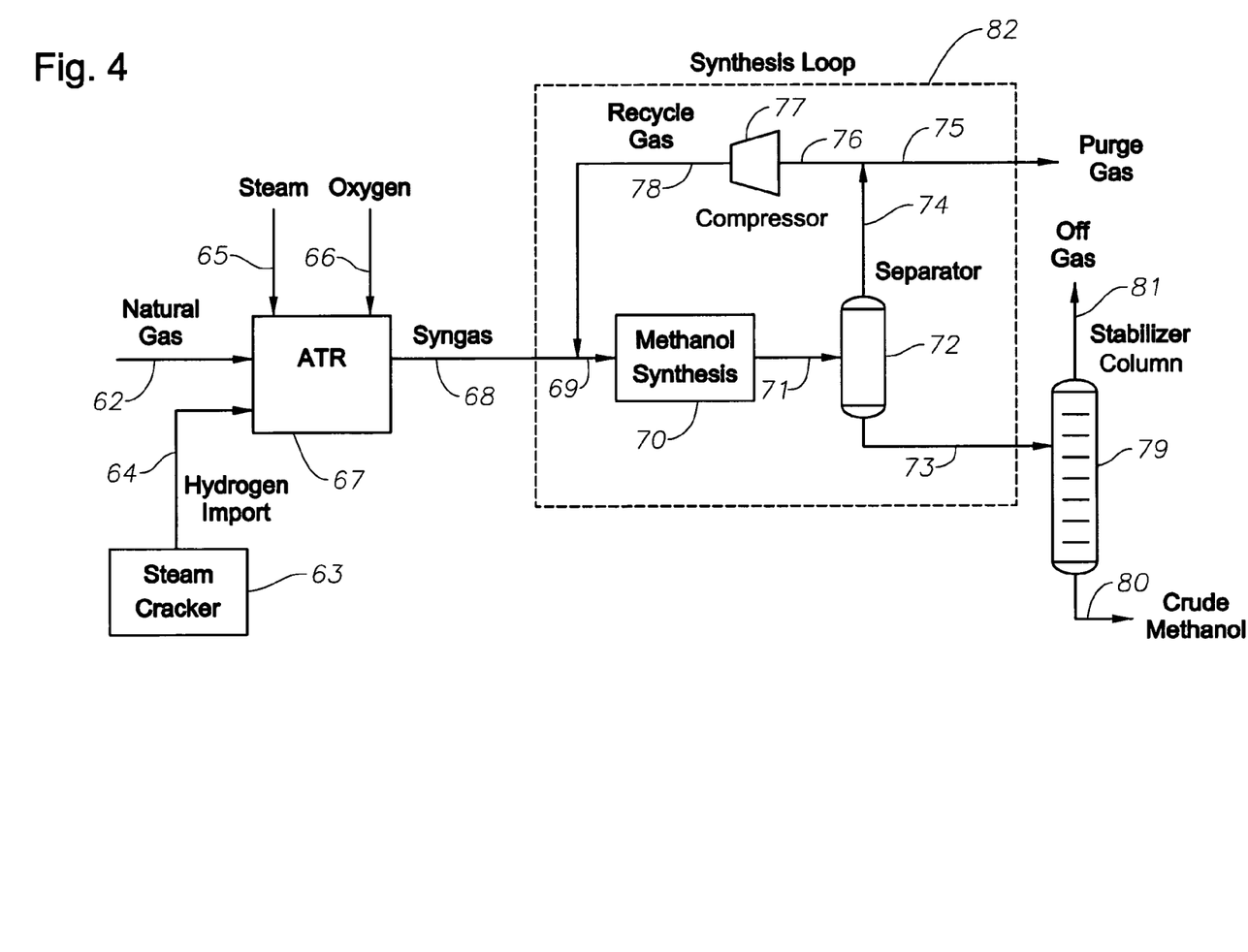
FIG. 4 shows one embodiment of the present invention wherein the hydrogen stream is derived from an external hydrocarbon conversion process and is fed to the reforming reactor.

This example is demonstrated in FIG. 4. The natural gas stream 62, the steam stream 65, the oxygen stream 66, and the hydrogen import stream 64 from a steam cracker 63 are fed into the reforming reactor 67, in this example an ATR. The syngas stream 68 exits the reforming reactor 67 and a recycle gas stream 78 merge to form stream 69, which is fed into the methanol synthesis reactor 70. The methanol product stream 71 is fed into a separator 72. The bottoms stream 73 is fed into a stabilizer column 79. The off-gas stream 81 is purged from the stabilizer column 79 and the crude methanol stream 80 is removed from the bottom of the stabilizer column 79. The tops stream 74 from the separator 72 is split into a purge gas stream 75 and a second stream 76, which is fed into a compressor 77, which forms the recycle gas stream 78. The synthesis loop 82 comprises the methanol synthesis reactor 70, the separator 72, the compressor 77, and all related streams as shown in FIG. 4.

In all cases, the natural gas feed rate, oxygen:carbon, and steam:carbon ratio in the reforming section are kept constant, and the molar rate of recycle syngas in the methanol synthesis loop is kept constant.

Having now fully described this invention, it will be appreciated by those skilled in the art that the invention can be performed within a wide range of parameters within what is claimed, without departing from the spirit and scope of the invention. Furthermore, those skilled in the art shall appreciate that the present invention may also be used in Fischer-Tropsch processes.

What is claimed is:

1. A method for producing synthesis gas for methanol synthesis, said method comprising the steps of:
   a. obtaining a hydrogen stream without a secondary purification step comprising greater than 10 mol % methane from a hydrocarbon conversion process;
   b. feeding into a reforming reactor:
      i) a feed gas comprising methane, which is reduced according to the level of methane in the hydrogen stream,
      ii) water in a sufficient amount to have less than 1.2 moles water per mole carbon in said feed gas,
      iii) oxygen in a sufficient amount to have from 0.4 to 0.8 moles oxygen per mole carbon in said feed gas, and
      iv) a first portion of said hydrogen stream;
   c. reacting said feed gas, water, oxygen and said hydrogen stream in said reactor at a pressure in the range of from 10-100 bars (1-10 MPa) to form a raw syngas at a temperature greater than 900° C. and comprising less than 3 mol % methane; and
   d. forming the synthesis gas for methanol synthesis having a stoichiometric number of from 1.9 to 2.3.

2. The method of claim 1, wherein the hydrocarbon conversion process is selected from thermal cracking, naphtha reforming, alkane dehydrogenation, and propane cyclization.

3. The method of claim 1, wherein said reforming reactor is an autothermal reformer.

4. The method of claim 1, wherein said reforming reactor is a partial oxidation reactor.

5. The method of claim 4, wherein the raw syngas is formed at a temperature greater than 1000° C.

6. The method of claim 1, wherein said synthesis gas has a stoichiometric number of from 1.95 to 2.15.

7. The method of claim 1, wherein said hydrogen stream comprises greater than 1000 mol ppm CO.

8. A method for producing an oxygenate stream comprising methanol, said method comprising:
   a. feeding said synthesis gas of claim 1 to a methanol synthesis reactor; and
   b. subjecting said synthesis gas to process conditions sufficient to form said oxygenate stream.

9. A method for producing a light olefins stream comprising:
   a. feeding said oxygenate stream of claim 1 to an oxygenate-to-olefins reactor; and
   b. subjecting said oxygenate stream to process conditions sufficient to form said light olefins stream.

10. A method for producing polyolefins comprising:
    a. providing a feed stream comprising the light olefins stream of claim 9 to a polymerization reactor; and
    b. subjecting said light olefins stream to process conditions sufficient to form said polyolefins.

* * * * *